United States Patent [19]

Silver et al.

[11] Patent Number: 4,937,323

[45] Date of Patent: Jun. 26, 1990

[54] METHOD AND APPARATUS FOR LIDC ENHANCED WOUND HEALING USING BIOCOMPATIBLE TISSUE INGROWTH IMPLANTS

[75] Inventors: Frederick H. Silver, Bangor, Pa.; Michael G. Dunn, Aberdeen, N.J.

[73] Assignee: University of Medicine and Dentistry of New Jersey, Newark, N.J.

[21] Appl. No.: 206,120

[22] Filed: Jun. 13, 1988

Related U.S. Application Data

[63] Continuation-in-part of Ser. No. 113,547, Oct. 26, 1987, Pat. No. 4,925,924, and a continuation-in-part of Ser. No. 875,827, Jun. 18, 1986, abandoned, which is a continuation-in-part of Ser. No. 843,828, Mar. 26, 1986, Pat. No. 4,703,108, which is a continuation-in-part of Ser. No. 593,733, Mar. 27, 1984, abandoned.

[51] Int. Cl.$^5$ .................. A61L 15/01; C07K 15/06; A61N 1/32
[52] U.S. Cl. .................. 530/356; 424/445; 514/801
[58] Field of Search ................ 424/445; 514/828, 801; 530/356

[56] References Cited

U.S. PATENT DOCUMENTS

| | | | |
|---|---|---|---|
| 3,893,462 | 7/1975 | Manning et al. | 128/421 |
| 3,915,151 | 10/1975 | Kraus | 600/13 |
| 4,233,965 | 11/1980 | Fairbanks | 600/14 |
| 4,461,300 | 7/1984 | Christensen | 128/419 F |
| 4,528,265 | 7/1985 | Becker | 435/172.1 |
| 4,556,051 | 12/1985 | Maurer | 600/14 |
| 4,674,482 | 6/1987 | Waltonen et al. | 600/14 |
| 4,817,594 | 4/1989 | Juhasz | 428/464 |

OTHER PUBLICATIONS

Alvarez, Oscar M. et al, The Healing of Superficial Skin Wounds is Stimulated by External Electrical Current, Journal of Investigative Dermatology, vol. 81, No. 2, 81:144–148, 1983.
Assimacopoulos, Dennis, Low Intensity Negative Electric Current in the Treatment of Ulcers of the Leg due to Chronic Venous Insufficiency, American Journal of Surgery, vol. 115, May 1968, pp. 683–687.
Assimacopoulos, Dennis, Wound Healing Promotion by the Use of Negative Electric Current, The American Surgeon, vol. 34, No. 6, Jun. 1968, pp. 423–431.
Bassett, C. Andrew L., The Development and Application of Pulsed Electromagnetic Fields (PEMFs) for Ununited Fractures and Arthrodeses, Orthopedic Clinics of North America, vol. 15, No. 1, Jan. 1984, pp. 61–87.
Brighton, Carl T. et al., A Multicenter Study of the Treatment of Non-Union with Constant Direct Current, The Journal of Bone and Joint Surgery, vol. 63-A, No. 1, Jan. 1981, pp. 2–13.
Carey, L. C. et al., Effect of Continuous Direct Electric Current on Healing Wounds, Surgical Forum, vol. 13, 1962, pp. 33–35.
Carley, Patrick J. et al., Electrotherapy for Acceleration of Wound Healing: Low Intensity Direct Current, Arch Phys Med Rehabil, vol. 66, Jul. 1985, pp. 443–446.
DeHaas, W. G. et al., Non-Invasive Treatment of Ununited Fractures of the Tibia Using Electrical Stimulation, The Journal of Bone and Joint Surgery, vol. 62-B, No. 4, Nov. 1980, pp. 465–470.
Frank, Cyril B. et al., A Review of Electromagnetically Enhanced Soft Tissue Healing, IEEE Engineering in Medicine and Biology Magazine, Dec. 1983, pp. 27–32.
Gault, Walter R. et al., Use of Low Intensity Direct Current in Management of Ischemic Skin Ulcers, Physical Therapy, vol. 56, No. 3, Mar. 1976, pp. 265–269.
Gensler, W., Electrochemical Healing Similarities Between Animals and Plants, Biophys. J., vol. 27, Sep. 1979, pp. 461–466.
Goodman, Reba et al., Pulsing Electromagnetic Fields Induce Cellular Transcription, Science 220, Jun. 17, 1983, pp. 1283–1285.
Grodzinsky, Alan J., Electromechanical and Physicochemical Properties of Connective Tissue, CRC Critical Reviews in Biomed. Eng., vol. 9, Issue 2, pp. 133–198, 1983.
Lavine, Leroy S. et al., Electric Enhancement of Bone Healing, Science, vol. 175, 1972, pp. 1118–1121.
Leaper, D. J. et al., An Experimental Study of the Influence of Magnetic Fields on Soft-tissue Wound Healing, The Journal of Trauma, vol. 25, No. 11, Nov. 1985, pp. 1083–1084.
Konikoff, Electrical Promotion of Soft Tissue Repairs, Ann. Biomed. Engng., vol. 4, 1976, pp. 1–5.
McLeod, Kenneth J. et al., Frequency Dependence of Electric Field Modulation of Fibroblast Protein Synthesis, Science, vol. 236, Jun. 12, 1987, pp. 1465–1469.
Murray, J. Clifford et al., Modulation of Collagen Production in Cultured Fibroblasts by a Low-frequency, Pulsed Magnetic Field, Biochimica et Biophysica Acta 838 (1985), pp. 98–105.
Schauble, Muriel K. et al., Inhibition of Experimental Tumor Growth in Hamsters by Small Currents, Arch Pathol. Lab Med., vol. 101, Jun. 1977, pp. 294–297.
Smith, James et al., The Effect of Electrical Stimulation on Wound Healing in Diabetic Mice, Journal of the American Podiatry Association, vol. 74, No. 2, Feb. 1984, pp. 71–75.

(List continued on next page.)

Primary Examiner—John Kight, III
Assistant Examiner—Carlos Azpuru
Attorney, Agent, or Firm—Weiser & Stapler

[57] ABSTRACT

A therapeutic method for treating wounds by dressing the wound with a biocompatible biodegradable collagen tissue product and applying Low Intensity Direct Current (LIDC) to the product. The devices of the invention include biocompatible biodegradable collagen tissue products having means for the application of LIDC to the dressed wound.

35 Claims, No Drawings

OTHER PUBLICATIONS

Spadaro, J. A., Electrically Stimulated Bone Growth in Animals and Man, Clinical Orthopaedics and Related Research, No. 122, Jan.-Feb. 1977, pp. 325-332.

Spadaro, J. A. et al., Bacterial inhibition by electrical activation of percutaneous silver implants, Journal of Biomedical Materials Research, vol. 20, 1986, pp. 565-577.

Wolcott, Lester E. et al., Accelerated Healing of Skin Ulcers by Electrotherapy: Preliminary Clinical Results, Southern Medical Journal, vol. 62, Jul. 1969, pp. 795-801.

Wu, K. T. et al., Effects of Electric Currents and Interfacial Potentials on Wound Healing, Journal of Surgical Research, vol. 7, No. 3, Mar. 1967, pp. 122-128.

Zimmerman, M. et al., The Electrical Stimulation of Bone using a Filamentous Carbon Cathode, Journal of Biomedical Materials Research, vol. 18, 1984, pp. 972-938.

METHOD AND APPARATUS FOR LIDC ENHANCED WOUND HEALING USING BIOCOMPATIBLE TISSUE INGROWTH IMPLANTS

This patent application is a continuation-in-part application of co-pending U.S. application Ser. No. 113,547 filed 10/26/87, now allowed and U.S. Pat. No. 4,925,9 issued 5/15 and U.S. application Ser. No. 875,827, filed 6/18/86, now abandoned, both of which in turn are continuations-in-part of U.S. application Ser. No. 843,8 now allowed and U.S. Pat. No. 4,703,108 filed 3/26/86 issued Oct. 27, 1987, which patent in turn is a continuation-in-part of now abandoned patent application Ser. No. 593,733 filed March 27, 1984.

The specification and disclosure of the above-identified patent applications are incorporated herein by reference in their entirety.

All the prior art to which reference has been made in the prior applications is explicitly referred to herein. In addition, a listing of the publications including patents, which are of interest and representative of the state of the art, appear further below.

BACKGROUND OF THE INVENTION

1. Field of the Invention

This invention relates to the field of wound treatment with electrical stimulation, particularly with Low Intensity Direct Current (LIDC). This invention also relates to biocompatible biodegradable collagen tissue products, especially sponges, used in combination with LIDC for the treatment of wounds.

This invention further relates to biocompatible biodegradable collagen tissue products which also comprise means for the application of LIDC in conjunction with wound treatment.

While great success has been obtained with the use of biocompatible collagen tissue implant products for the healing of wounds, the use of LIDC stimulation in combination with these collagen tissue implants indicates that the healing function of the implants is accelerated by LIDC stimulation. Such acceleration of the healing of these implants is highly desirable and expands the clinical uses for these products. As described in greater detail hereinafter, the compositions of this invention comprise biocompatible biodegradable collagen products, especially sponges, having electrodes for the application of LIDC stimulation to a wound site being treated with the collagen tissue implant.

2. Objects of the Invention

An object of the invention is to provide therapeutic methods and products for treating wounds, especially of humans, which comprise continuously treating the wound with an implanted collagen product together with LIDC stimulation to promote the in-growth of fibroblasts from surrounding tissues into the implanted product as well as the alignment of collagen fibers in relation to the implant, thereby improving healing, tissue organization, new tissue formation and the assimilation of the implanted product. The invention provides various useful products for such purposes.

Another object of the invention is to provide a method for promoting optimum tissue ingrowth into biocompatible biodegradable implanted collagen products employing LIDC stimulation. An object of the invention is to provide materials for skin and other tissue implants which have all the characteristics of living tissue for applications inside wounds or outside of the body, having a means for the application of LIDC stimulation to the tissue implant healing site.

An object of the invention is to provide several new products and compositions and make available methods of treatment which are a significant contribution to the medical and healing arts. The listing of objectives provided herein, or of features of the invention, is not intended to be exhaustive, but merely illustrative. Other objects will become apparent to one of average skill in the art in the further description of the invention.

3. Brief Description of the Prior Art

Wound repair involves cellular events such as cell migration, replication, synthesis and deposition of new connective tissue, remodeling and epidermal cell migration over dermal repair tissue. Many studies (1–7) suggest that these events may be influenced by endogenous and exogenous electric or magnetic fields in both soft and hard tissue.

Collagenous matrices have been shown to delay contraction of dermal animal wounds (8), coordinate the deposition of organized dermal repair tissue (9) and act as a support for cells in culture (10). Collagen matrices containing hyaluronic acid and fibronectin increase fibroblast migration and proliferation and improve the deposition of organized repair tissue in both an animal model and in cell culture (10, 11).

Electrical stimulation using direct electrical currents or induced voltages and currents has been shown to affect wound healing (12–23). Typical methods for the use of electric current in the promotion of healing are those methods employing low intensity direct current (LIDC) and, more recently, pulsed electromagnetic fields (PEMF). A recent overview summarizing research conducted on both methods was published in *I.E.E.E. Engineering in Medicine and Biology* in 1983 (32).

Electric current was initially employed to promote the healing bone fractures, especially those fractures demonstrating non-union. A discussion of the electromechanical and physiochemical properties involved was published by Grodzinsky in 1983 (3). An overview of electrically stimulated bone healing was published by Spadaro in 1977 (33).

The use of PEMF's to treat ununited bone fractures was described by DeHaas in 1980 and Bassett in 1981 in the *Journal of Bone and Joint Surgery* (12, 14). The use of LIDC to promote bone healing was described by Lavine in *Science* in 1972 (15). The article described the successful repair of a prominent pseudarthrosis defect in a 14 year old child through current applied via a platinum electrode. It was not disclosed whether the wound electrode was a cathode or anode.

Brighton in 1981 (13) published the results of a study of the treatment of 186 patients suffering from non-union of bone fractures with LIDC of 20 microamps placing the cathode on the wound site. A four cathode stainless steel electrode was used to apply the current. Zimmerman, in 1984 (34), described the use of 1–20 microamp cathodic LIDC for the stimulation of bone growth. The current was applied using filamentous carbon fibers.

Several patents have issued for methods and devices for the use of PEMF's to promote bone healing. U.S. Pat. No. 3,915,151 issued to Kraus describes a magnetic coil device for the induction of electric current by the application of a magnetic field to injured bones and related soft tissues. U.S. Patent No. 4,233,965 issued to Fairbanks describes a similar method and device using PEMF's to induce an electric current for the healing of bone and connective tissue, improved to achieve a deeper penetration of electrical current, especially for the treatment of arthritis.

U.S. Pat. No. 4,556,051, issued to Maurer describes a device and method for promoting the healing of fractured bones and related connective tissue through the simultaneous application of PEMF's and pulsed electric current in a fixed phase relationship to produce a net current in the region of the fractured bone generally perpendicular to the plane of the fracture. U.S. Pat. No. 4,674,482 issued to Waltonen, et al describes a method and device for the promotion of vasoconstriction through the application of PEMF's. The inventor describes the device as an "electric icepack." A biasing circuit is described that prevents the occurrence of a reverse polarity pulse upon the fall of the magnetic flux induced by the fall of the generated pulse, thereby diminishing high frequency ringing at the beginning of a treatment signal and improving the promotion of vasoconstriction.

U.S. Pat. No. 4,461,300 issued to Christiensen describes a method and device employing cathodic LIDC to promote the healing of fractures and injuries to bones and related soft tissues. A specifically designed cathodic electrode implant assembly with a particular method of implantation at the fracture or bone defect site is disclosed.

The above patents and articles do not disclose the method and device of the present invention to promote the healing of muscle and skin tissue, nor do they describe the use of electric current in conjunction with biocompatible synthetic or collagen tissue ingrowth implants to promote healing.

One other patent of interest is U.S. Pat. No. 3,893,462 issued to Manning, which describes a method and device employing an undulating electrical signal having a wave form whose rise time differs from its fall time, in turn producing a voltage at the tissue level that is bipolar with the amplitude and frequency components of one polarity differing from those of the opposite polarity, effecting the bioelectrical signals at the cellular or tissue level, thereby artificially stimulating the healing of the cells and/or tissue. This significantly differs from the steadily applied LIDC method and device of the present invention, even when the tissue ingrowth implants are not considered.

As regards the healing of muscle and skin wounds, a discussion of the bioelectric phenomena involved in such wound healing was published by Wu, et al in 1967 (31). The prior art discloses both the use of PEMF's and LIDC's to promote healing.

With respect to PEMF's, Bassett, in a 1984 article published in *Orthopedic Clinics of North America* (35), discloses that when a dynamic, magnetic field passes through a static conductor, such as wound tissue, an electric field is induced in the conductor, with voltages of 1.0 to 1.5 millivolts per centimeter. Bassett states that the current induced varies with time, unlike the steady current applied in the present invention. Bassett suggests that PEMF's promote collagen growth. Goodman, in a 1983 article published in *Science* (36), describes the stimulation of messenger RNA specific activity by PEMF's of 0.1 G per micro second. Murray, in a 1985 article published in *Biochimica et Biophysica Acta* (6) describes the increase in collagen production in cell cultures produced by low frequency PEMF's. The field was generated by a generator-driven pair of Helmholtz-aiding air cored coils. Leaper, in a 1985 article published in the *Journal of Trauma* (37), on the other hand, disclosed that a 400 Gauss magnetic field was found not to promote wound healing.

A 1987 article by McLeod in *Science* (7), describes the use of AC electric fields of 0.1–1000 Hz frequency to promote proline incorporation into fibroblast populated collagen matrices.

As early as 1962, the use of LIDC's to promote wound healing was described by Carey (30). Currents of 200 to 300 microamps were described, introduced by stainless steel electrodes. Unlike the present invention, the cathode was disclosed to attract inflammatory agents. Two articles by Assimacopoulos, published in 1968 (16, 21), described the use of currents with the anode at the wound site to promote wound healing. Currents of 50–1000 microamps were applied via flexible surgical steel gauge electrodes, and resulted in scar formation of dense connective tissue rich in hyalinized collagen fibers, parallel to the skin surface. Wolcott, in 1969 (22), described that the use of 200–1000 microamp LIDC applied through copper mesh electrodes packed in gauze soaked with conductive medium promoted the healing of ischemic skin ulcers. The polarity of the electrode was reversed whenever the rate of healing plateaued. Wolcott suggested that the anodic current did not promote healing but instead provided a rest period for clearance of metabolic wastes.

Konikoff, in 1976, (18), also described the use of 20 microamp LIDC to promote soft tissue repair. Konikoff applied the current with platinum electrodes. Gault also reported in 1976 that 200 to 1000 microamp LIDC would promote the healing of skin wounds (23). The current level was recommended at a level that was not so low as to permit copious serous drainage, nor so high as to cause blood exudate. The electrodes, the materials for which were not disclosed, were sandwiched between four layers of gauze with Ringer's or normal saline solution used to provide conductivity. The treatment was applied two hours on, four hours off, twice a day, several days a week. The cathode and anode were reversed after three days.

Schauble described in 1977 (17), the use of anodic and cathodic LIDC between 1 and 3000 microamps to inhibit tumor growth and reduce metastasis. Both steel and silver electrodes were used at high levels of current to produce tumor necrosis. Gensler published in *Journal of Biophysics* in 1979, a comparison of the electrochemical healing similarities between animals and plants (38). Alvarez, in 1983, described the use of 50–300 microamp anodic LIDC to stimulate the healing of superficial skin wounds (19). The current was applied with silver-coated electrodes. Smith (20), described the application of 10–20 microamp LIDC through a Gilson ICT-5 stimulation apparatus to stimulate the healing of skin wounds. He did not disclose whether the current was anodic or cathodic or the electrode material employed. Carley, in 1985 (39), described the use of 200–800 microamp LIDC to promote wound healing. Devices using both stainless steel and carbon mesh electrodes were used. Current was applied for two hours and discontinued for two to four hours, twice a day three times a week. Before the current was applied, the wound was irrigated with saline and packed with saline dampened gauze or absorption gel, serving as an interface with the wound for the electrode. Carley also described the switching of electrode polarity whenever the rate of wound healing would reach a plateau.

Spadaro in 1986 (40), disclosed the inhibition of bacterial growth in wounds by the application of 5-100 microamp anodic LIDC through percutaneous silver implants. It has also been reported by Cheng et al (41) that water molecules may be protonated at the anode and deprotonated at the cathode and lead to pH changes depending on current density. Brighton et al (42) attributed deposition of bone near the cathode to decreased oxygen tension.

The LIDC and PEMF methods of the earlier research differ significantly from the method and device of the invention described herein. None of the earlier publications describe the use of electric current or electromagnetic force in conjunction with biocompatible synthetic or collagen tissue ingrowth implants. None of the earlier publications describe the use of such materials to promote healing, tissue organization or new tissue formation.

While it was known that such currents or electromagnetic forces stimulated healing in the body's own tissues, it was unexpected that the application of LIDC stimulation would additionally promote the ingrowth of fibroblasts into the collagen implants.

SUMMARY OF THE INVENTION

The invention comprises using implantable biodegradable biocompatible collagen tissue products that coordinate the deposition of organized repair tissue in combination with the application of LIDC stimulation to promote wound healing.

The invention also comprises a method of applying LIDC stimulation to the implanted products to accelerate the deposition of wound tissue materials such as fibroblasts and collagen in the implant, thereby accelerating the assimilation of the implant into the surrounding tissues.

The biocompatible biodegradable collagen tissue products may comprise a collagen sponge prepared from collagen powder particles of uniform size, the sponge comprising a matrix containing pore-type channels each connected to the surface and channels connecting the pore-type channels to each other. The collagenous implants may also be prepared from collagen flake particles, of non-uniform size, also forming a collagenous matrix of the two types of pores and channels. However, the flake implant channels and pores are larger and less uniform in diameter. A flake implant also comprises a greater number of these channels and pores, and hence a larger surface area. This causes difficulties in incorporating an electrode-type means for the application of LIDC stimulation into the collagen product.

The biocompatible biodegradable tissue product need not be made from collagen, any other biocompatible synthetic polymer may be used. The collagen sponge matrices are preferably cross-linked and most preferably contain fibronectin (FN) and/or hyaluronic acid (HA), which enhance wound healing by increasing the quantity of fibroblasts and the deposition of collagen during tissue ingrowth, thereby promoting the organization of collagen fibrils into fibers.

The preparation of collagen products with HA and/or FN is disclosed in the parent application Ser. No. 875,827 which is in this respect incorporated by reference.

In accordance with the invention, the implantable, biodegradeable biocompatible collagen tissue products that coordinate the deposition of organized repair tissue comprise a means for the application of LIDC stimulation to the wound healing site. In accordance with the invention, the means for the application of LIDC stimulation may comprise a biocompatible electrically conductive inert electrode, which is then removed once the maximum acceleration of healing by LIDC stimulation has been attained. A number of traditional electrode materials function in a biocompatible electrically conductive manner, typically carbon and metals, including the noble metals. The electrode can be in any suitable physical form such as in the shape of a wire, plate, mesh and the like. The invention also contemplates the use of a biodegradable tissue-compatible electrode for the application of LIDC, which then would not be removed, but permitted to degrade as the wound heals. The invention also contemplates a dispersion of metal particles or a solution of an electrolyte in the collagen implant to render the implant electrically conductive so that it functions as a combination wound dressing and electrode for the application of LIDC stimulation. By definition, all of the above embodiments are referred to as electrically conductive implants.

In accordance with the invention, the preferred system by far is one in which the means for applying LIDC stimulation is cathodic. The current is preferably at least 20 microamps, up to 100 microamps and higher.

In accordance with the invention, it is preferable by far that the collagenous or synthetic polymer implant comprising a means for the application of LIDC stimulation is formed of powder particles. Such a sponge implant, having less pores and channels of more uniform size than a flake product provides an implant better able to accommodate an electrode.

It is also in accordance with the invention that the electrically conductive implant formed from either type of collagen implant for the application of LIDC stimulation be used in combination with the dressing of a wound with collagen powder or flake particles, the collagen particles being applied first and the electrically conductive implant being placed on top of it. The constitution of the collagen product dressing used at the beginning of the treatment is not necessarily the same as the constitution of the collagen product used later in the treatment. Its constitution is that which is recommended by accepted medical practice.

The methods and compositions of the invention are useful to promote the healing of wound tissues associated with burns, skin ulcers, and other injuries or diseases, both internal and external. The methods and compositions of the invention are also useful for tissue reconstruction, including cosmetic surgery. The methods and compositions of the invention are useful in the treatment of both humans and animals.

BRIEF DESCRIPTION OF THE DRAWINGS

FIG. 1 shows a plot of the number of fibroblasts per square millimeter versus direct current stimulation in microamps and electrode polarity for implanted collagen sponges containing carbon fibers six days post-wounding.

FIG. 2 shows a light micrograph of the cathode region of 100 microamp stimulated collagen sponge containing carbon fibers at day six post-implantation on an excised guinea pig dermal wound.

FIG. 3 shows a diagram of the method used to fabricate the collagen sponge containing carbon fiber electrodes.

FIG. 4 shows an illustration of the method used to implant collagen sponge with carbon fiber electrodes on a full thickness excised wound on the back of the guinea pig.

FIG. 5 shows a light micrograph of unstimulated collagen sponge (arrow) containing carbon fibers six days post-implantation on a guinea pig excised dermal wound. Bar shown equals 50 micrometers.

FIG. 6 shows a light micrograph of the anode region (A) in the collagen sponge of FIG. 4. Bar equals 50 micrometers.

DETAILED DESCRIPTION OF THE INVENTION

As stated above, soft tissue wound repair has been shown to be accelerated by LIDC stimulation. The accelerating effects of electrical stimulation on wound healing may be a consequence of: (1) modification of endogenous bioelectricity, (2) activation or attraction of inflammatory cells, (3) the presence of electrode breakdown products, (4) attraction of connective tissue cells, (5) enhanced cell replication, (6) enhanced cellular biosynthesis or (7) inhibition of proliferation of infectious microorganisms. The prior art discussed above generally describes the use of LIDC solely to accelerate the healing and regeneration of the body's own soft tissues.

As was also discussed above the healing of soft tissue wounds has additionally been shown to be promoted by biocompatible biodegradable collagen tissue implants that coordinate the deposition of organized dermal repair tissue. These include collagen powder sponge implants as discussed in the above-referenced pending U.S. application Ser. No. 875,827 and collagen flake implants as disclosed in the above referenced pending U.S. application Ser. No. 113,547.

It has now been discovered that the application of LIDC stimulation to such collagen implants, particularly continuous stimulation, accelerates the soft tissue wound healing promoted by those implants. The application of continuous LIDC stimulation of at least 20 microamps and up to 100 microamps to these implants, especially collagen sponge products, has been shown to accelerate the deposition of wound tissue materials such as fibroblasts and collagen in the implant, thereby accelerating the assimilation of the implant into the surrounding tissues.

The wound healing properties of implantable collagen sponges used in combination with LIDC stimulation have been demonstrated. By definition, a collagen sponge is a collagen implant prepared from collagen powder particles further defined below. Healing as measured by fibroblast ingrowth occurs by cathodic LIDC stimulation using currents as high as 100 microamps.

Experiments were conducted using a well characterized guinea pig full thickness excised wound model and an LIDC stimulated collagen powder sponge. In one series, the sponge contained both an anode and a cathode. Two wounds were prepared on guinea pigs, and were dressed with collagen powder sponges, one of which received up to 100 microamps LIDC stimulation thereough a carbon fiber electrode in the sponge and one of which did not, as a control. In a second series two wounds were prepared on guinea pigs and were dressed with collagen powder sponges, one of which received up to 100 microamps anodic LIDC stimulation, and one of which received up to 100 microamps cathodic LIDC stimulation. Both were applied through a carbon fiber embedded in the sponge.

The physical structure of the collagen sponge and its wound healing properties have been characterized in previous studies (9, 11, 25 and 29) as well as in the parent patent and applications, already incorporated herein by reference. As disclosed in the patent and applications, two types of collagen particles are used to form the collagen implant, powder and flakes. The powder forms a collagen sponge matrix having surface and interior pores that are connected by channels within the interior of the sponge. The pores and channels are generally of uniform size between about 50 and about 250 micrometers in diameter. By their very nature, the powder particles are essentially uniform in size, and capable of passing through a 40 mesh screen.

The flakes, on the other hand, form a collagenous matrix with a greater number of larger pores and channels of a non-uniform diameter up to 300 micrometers. The non-uniform diameter of the pores and channels is a function of the flakes comprising particles non-uniform in size with essentially none of the particles being powder particles capable of passing a 40 mesh screen. By definition, the flake particles are 0.1 to 3.0 cm in length, commonly about 1.0 cm, the majority of which, or over 50%, will pass through a 10 to 30 mesh screen. Preferably over 80% to about 100% of the flakes will pass through a 10 to 30 mesh screen. Flake particles produce an implant with a surface area markedly greater than powder particle implants, from at least about 20% to at least about 50% or even to about 80% greater.

In the present invention, carbon fibers were used as the implant electrodes to eliminate the influence of metal ions on inflammation and granulation tissue deposition. Carbon fibers are inert and do not release metallic ions. The carbon fiber electrodes are surgically removed once the wound heals. LIDC's up to 100 microamps were employed because they could be delivered with a battery pack for a period of up to seven days.

However, the electrode materials of the present invention are not necessarily limited to carbon. Practically any inert biocompatible electrically conductive material may be used. Electrodes may be used comprising metals such as steel, particularly stainless steel and noble metals such as gold, silver, platinum and palladium. In addition to wires the electrodes can also be in the form of a plate or wire mesh.

Electrodes may also be used comprising biodegradable tissue-compatible electrically conductive materials to eliminate the need to remove the electrode after the implant has been assimilated and the wound has healed. Instead, the electrode would be permitted to dissolve.

Furthermore, the means of applying LIDC stimulation to the wound-implant interface is not necessarily limited to electrodes. Ingredients may be added to render the implant electrically conductive and eliminate the use of an electrode within the implant. The LIDC stimulation would be applied externally and the implant itself would conduct the current to the wound-implant interface.

The implant can be rendered electrically conductive by dispersing biocompatible electrically conductive materials through the implant during the manufacturing process. Suitable biocompatible electrically conductive materials are typically particles of metals such as the metals appropriately used for electrodes in this invention. This includes stainless steel and the noble metals such as gold, silver, platinum and palladium. The more electrically conductive the material, the lower the quantity that needs to be dispersed in the implant.

The implant can also be rendered electrically conductive by adding to the collagen formulation an electrolyte, typically an electrically conductive ionic salt solution. Typical electrolytes include salt solutions of metal ions such as silver, iron, calcium, sodium and potassium. It is contemplated that electrical conductivity can be achieved by adding to the collagen mixture when the implant is being manufactured a silver nitrate solution of between about 0.1 and 3.0 M. The same results can be expected of potassium chloride solutions of the same concentration.

Experiments were first conducted with the anode and cathode close together (first generation device) and then separated (second generation device) to evaluate the possibility of synergism between the effects of the two electrodes. For both devices the fibroblast density near the cathode was significantly higher at a 100 microamp current than that observed in controls. In the second generation device at the anode the number of fibroblasts was significantly lower than that of controls, indicating the fibroblast ingrowth into the collagen sponge is enhanced by cathodic stimulation.

A clear trend is observed if the number of fibroblasts within the collagen sponge are plotted versus stimulation current and polarity (see FIG. 1). Cathodic stimulation of 100 microamps results in about 41% more fibroblasts in the collagen sponge after 6 days. According to histological evidence (see FIG. 2), fibroblasts near the cathode were oriented parallel to the direction of the electric field and layed down collagen fibers that were aligned in the direction of the field. No differences are observed in the number of fibroblasts in the sponge that are found near the circuit connector compared with areas away from the connector. In comparison, the anode at 100 microamps appeared to attract inflammatory cells possibly due to an electrophoretic effect.

Increased numbers of fibroblasts seen in cathodic stimulated collagen sponges may reflect the effect of electrical current on cell migration or may be a result of changes at the electrodes of factors such as oxygen tension and pH. In addition the increased fibroblast count may reflect the effect of electrical current on cell migration. Increased alignment of collagen fibers deposited by fibroblasts may reflect the alignment of axially oriented pairs of charged residues on collagen with the electric field.

The results indicate that fibroblast migration and collagen fiber alignment are enhanced in dermal wounds stimulated with direct currents between 20 and 100 microamps. The anode was observed to attract inflammatory cells and it is for this reason that the preferred system by far is one in which the means for applying LIDC stimulation is cathodic. In the products of the invention having electrode means for the application of LIDC stimulation, the electrodes function as cathodes and are defined for purposes of this invention as cathodes. Cathodic stimulation, using a collagen sponge and inert carbon electrodes, significantly enhanced wound healing.

The effectiveness of the wound repair increases as the cathodic stimulating current is increased. The minimum LIDC current is that smallest flow rate effective to accelerate the healing function of the biocompatible synthetic or collagen implant at a clinically observable rate, generally about 1.0 microamp. Preferably the LIDC current is at least about 20 microamps to about 100 microamps, and greater, up to a current that does not demonstrate any increased effectiveness in the healing function of the biocompatible synthetic or collagen implant.

The effectiveness of wound repair also increases as the duration of the cathodic stimulation is increased. The minimum duration of LIDC stimulation is the minimum time period necessary to produce a clinically observable improvement in wound healing. As would be expected, this varies with the intensity of LIDC current applied, and can range from several minutes to an hour. Although the treatment can be discontinued at any time with a showing of improvement in wound healing, the LIDC stimulation is preferably applied continuously until maximum healing is achieved. Again, this depends upon the intensity of LIDC current applied, as well as the severity of the wound, and can take from several days to several weeks.

In another embodiment of the invention, the LIDC stimulated collagen implant is prepared from collagen flakes. However, as stated above, collagen powder sponge products are preferred by far in implants having electrodes. The less concentrated uniform size sponge pores better accommodate the electrodes than do flake implants having a greater amount of non-uniform pores.

In another embodiment, the collagen sponge is crosslinked, as disclosed in parent application Ser. No. 875,827 which has already been incorporated herein by reference. In still another embodiment the collagen sponge, crosslinked or non-crosslinked, also comprises HA and/or FN to enhance wound healing. As stated above, HA and FN enhance wound healing by increasing the quantity of fibroblasts and the deposition of collagen during tissue ingrowth, thereby promoting the organization of collagen fibrils into fibers.

The preferred concentration of both HA and FN in a collagen sponge is from about 0.1% by weight to about 4% by weight for each compound. More preferably, the range is from about 1% to about 2% for each component. Most preferably, the sponge contains about 1% each of HA and FN.

In another embodiment, the powder or flake collagen implant does not comprise internal electrodes. Rather, the LIDC stimulation is applied externally to the wound dressing.

It is within the scope of the present invention that the constitution of the collagen product used at the beginning of treatment not necessarily be the same as the constitution of the collagen product at the end of treatment. Depending upon the nature of the wound, treatment may begin with a collagen flake implant that is replaced by a combination flake-powder implant. This implant may be replaced by a series of implants in which the powder content is progressively increased, to a point at which treatment is concluded with a pure powder implant.

Likewise treatment may also begin with a collagen powder implant that is progressively replaced by powder and flake implants of increasing flake content to a point at which treatment is included with a pure flake implant. Treatment may also begin with a combination collagen flake and powder implant that is replaced by implants with progressively increasing flake or powder content.

It is also within the scope of the present invention that before the collagen implant is applied, the wound is first dressed with collagen powder or flakes or both, with the implant having a means for the application of LIDC stimulation then being placed on top of this dressing.

It is within the scope of the present invention that biocompatible synthetic polymers also be used to form the implants.

As disclosed in the parent patent and applications, and in the literature, the powder and flake products used in the invention may contain any number of additives that are conducive to the healing of wounds, such as hormones, bactericides, growth promoters, immunogens, antibiotics and the like.

The following examples and illustrations are not intended to be a limitation on the invention, but are intended to be, and are merely, illustrative. One skilled in the art will readily be able to make variations in the various procedures illustrated below without departing from the spirit of the invention.

MATERIALS AND METHODS COLLAGEN SPONGE—ELECTRODE PREPARATION

Collagen sponges containing carbon fiber electrodes were prepared using the following procedures. Pairs of small holes were punched on opposite sides of a styrene plastic tray (Clear-View Packing, Inc., Clifton, N.J.). The dimensions of the tray used to form collagen sponges were 12×8×1 cm. Trays were placed on a piece of plywood and each hole on the tray was lined up with a nail on the plywood. The nails were spaced every 1.0 cm on the plywood as diagrammed in FIG. 3. A twisted braided tow of uncoated and unsized carbon fiber containing 3,000 individual filaments of approximately 7 micrometers in diameter (Hercules, Wilmington, DE) was threaded onto a large needle, passed through distilled water and threaded through the holes in the tray (see FIG. 3). When the entire tray was threaded, the fiber tow was pulled taut and tacked down. The process resulted in parallel carbon fibers separated by 1.0 cm. in the plastic tray.

Insoluble collagen type I from fresh uncured bovine corium was obtained from Devro, Inc. (Somerville, N.J.). The corium was limed, fragmented, swollen in acid, precipitated, washed with distilled water and isopropanol, lyophilized and stored at −30° C. (24). Collagen was characterized by sodium dodecyl sulfate polyacrylamide gel electrophoresis and amino acid analysis as typical of type I collagen without noncollagenous protein contamination (25).

A 1% (W/V) dispersion of type I collagen in dilute HCL pH 2.0 was prepared and mixed for 2 minutes at room temperature at high speed using a blender as previously described in (26). Seventy milliters of the deaerated dispersion was poured into each plastic tray and air bubbles were removed by placing the tray in an oven at a vacuum of less than 0.4 millitorr at room temperature. The plastic tray containing the dispersion was cooled to −30° C. for at least three hours and the frozen dispersion was lyophilized until dry.

The sponge was removed from the tray and crosslinked by severe dehydration using a process termed dehydrothermal crosslinking (DHT) at a temperature of 110° C. and vacuum of less than 0.4 millitorr for three days. The sponge was further crosslinked by placing it in a 1% (W/V) solution of cyanamide for 24 hours at pH 7.2 (26) and then it was washed thoroughly with at least three charges of distilled water over a 24 hour period. The final step was to freeze and then lyophilize the sponge.

A 2 cm width was cut from the 3 mm thick sponge, and excess carbon fibers were dissected off the strip under a dissection microscope, and blown off with air. From this strip, a 2 ×2 cm piece of sponge was cut, with free carbon fiber ends of about 1.0 cm length outside of the sponge. Using a crimping tool and solderless connectors, both of the two free carbon ends were connected to a 5 cm piece of insulated wire (with the ends stripped). Male/female connectors were soldered to the other end of these wires. A thin coating of medical grade silicone (Dow-Corning) was spread over the "air side" of the sponge to act as a moisture barrier for the graft and to provide a tough surface through which anchoring sutures could be applied (see FIG. 4). Silicone was also used to electrically insulate the crimped connectors at the wire/carbon fiber interface. Sponges and connectors were sealed in a plastic bag and sterilized by exposure to 2.5M rads of gamma radiation.

DC STIMULATOR CIRCUIT CONSTRUCTION

The stimulation circuit was designed to deliver a constant, adjustable direct electric current (DC) (27). The circuit was a variable current regulated voltage source (9 volt). The current could be set from 1–100 microamps via a potentiometer, and was unaffected by changes in the load resistance within a range of between 0 and approximately 100K ohms. The circuit components were taped onto the power source. The cathode lead wire was connected to the negative side of the battery and the anode connected to the transistors.

ANIMAL STUDIES—FIRST GENERATION DEVICE

Female (500–1,000 g) Albino Hartley guinea pigs (Perfection Breeders, Douglassville, PA) were depilated one day before surgery by applying a depilatory cream (Nair). The day of surgery guinea pigs were anesthesized by injection of Xetamine (Vetalar, Parke Davis) at 35 micrograms/g body weight and Xylazine (Rompun, Bayret) at 5 micrograms/g body weight. The shaved and depilated back of the guinea pig was disinfected with several washes of alcohol and Povidone. Surgery was performed under sterile conditions. A full thickness, 2×2 cm square of skin including the panniculus carnosus was removed from one side of the back via careful dissection with a scalpel, and hemostasis was achieved. The collagen/carbon sponge was wetted with sterile saline for ten minutes and then placed into the wound, with the silicone side up. Catgut stitches were applied to secure the sponge in place. The procedure was repeated for a duplicate wound on the opposite side of the spine. One wound was randomly chosen to receive electrical stimulation, and the male/female connectors at the end of the electrode wires were attached to the circuit; one wound served as an unstimulated control. The control device consisted of a collagen sponge containing collagen fibers that were connected to a device without a battery. The wounds were wrapped with sterile gauze, then the circuitry was fixed on the back with Elastikon elastic tape (Johnson and Johnson).

Currents of 20 and 100 uA were studied in this model. The current was checked daily by measuring the voltage across the 1K ohm resistor via test leads. Current levels remained unchanged during the experiment.

The current density was estimated to be in the range of 1.5 to 15 uA/cm$^2$ and 8 to 80 uA/cm$^2$ for current levels of 20 and 100 uA, respectively. The higher value of current density for each current level was obtained by assuming that the carbon fibers act as a solid electrode 1 mm in radius while the lower value for each current level was obtained by assuming that the current was delivered from the surface of 3,000 individual carbon fibers 7 um in diameter.

ANIMAL STUDIES—SECOND GENERATION DEVICE

In the second generation device, two collagen sponges were implanted in the same manner as described above for the first generation device, however each sponge contained only one active electrode; the outer electrode of the two in the sponge was activated. The anode and cathode were randomly chosen to be in the left or right sponge and in this instance there was no control sponge on the animal. The wounds were wrapped with Elastikon tape as described above for the first generation device.

Six days after implantation of a first or second generation device the guinea pig was anesthesized, and the bandages were carefully removed. The distance between the electrodes was measured. The current through the stimulated wound was determined with a Volt/Amp/Ohm meter (Radio Shack). Both of the sponges (control and stimulated) were removed from the animal by dissecting around the wound and the material was placed in Carson's Fixative. The carbon fiber electrodes and silicone layer were carefully removed (and saved for SEM) and the collagen sponge was divided into four equal squares. The specimens were marked cathode 1, 2 and anode 1, 2 where sample 1 was closest to the electrode and sample 2 was from the distal portion of collagen sponge. These 4 regions were then prepared for histological evaluation.

LIGHT MICROSCOPY

Fixed specimens were processed using routine paraffin embedding and tissue sectioning procedures. Tissue sections were stained with Hematoxylin and Eosin (H&E) or picrosirius red (28).

The extent of wound tissue deposition in the collagen sponge was qualitatively examined by examining H&E stained sections under a Leitz Laborlus 12 light microscope. Neovascularization, fibroblast proliferation, collagen deposition, and the inflammatory and foreign body responses were noted. Light micrographs were taken with a Leitz 35 mm camera, with the long axis of the micrograph corresponding to the direction of the electric field between the electrodes, in order to determine the number of fibroblasts/mm$^2$. Cells were considered fibroblasts if they had an elongated nucleus and elongated shape. For the electrically stimulated collagen sponges, fibroblasts were counted at a magnification of 100 in the region between the electrodes near the cathode, (a), and near the anode, (b).

RESULTS

These studies were directed at evaluating the effect of LIDC stimulation on repair tissue in a well characterized skin excision model. In this model the collagen sponge is infiltrated by fibroblasts and capillaries resulting in the deposition of organized collagen fibers and formation of new vasculature as described previously (9, 11, 29).

Controls consisted of collagen sponges containing carbon fibers that were connected to a wire without a circuit. Control devices were implanted on excised dermal wounds. Sponges in control devices were infiltrated by day six post-implantation with unoriented fibroblasts (see FIG. 5). Tissue ingrowth was often accompanied by a slight foreign body reaction near the collagen sponge. The foreign body reaction consisted of accumulation of inflammatory cells. The number of fibroblasts/unit area at day 6 was observed to be 125±18 (see Table 1) for unstimulated sponges.

The electrodes (cathode and anode) in the first generation prototype were separated by 1 cm. At a current of 20 microamps the repair tissue within the collagen sponge appeared visually to be denser than in the control. Dense ingrowth of fibroblasts and capillaries was noted near the anode. No evidence of a foreign body reaction was observed. The number of fibroblasts ranged from 130±14 to 156±13 at the cathode and anode, respectively (see Table 1).

At a current of 100 microamps using the first generation device, anode and cathode regions appeared distinctly dissimilar. The cathode region was well infiltrated with oriented, mature fibroblasts. However, the anode region was well infiltrated by neutrophils. Fibroblast infiltration was increased significantly (at a 95% confidence level) at the cathode region compared with controls.

A second generation device in which the electrodes were in separate sponges (distance between electrodes=3 cm) was studied at a current of 100 microamps to evaluate the effects of the anode and cathode independently. The cathode region was similar in appearance to the cathode region in the first generation device stimulated with 100 microamps, but the sponge had dense oriented fibroblasts (see FIG. 2). In comparison, the sponge containing the anode contained numerous neutrophils (see FIG. 6) which were grossly visible as pus at sacrifice at six days. Fibroblast infiltration was maximized at the cathode (183±43) and minimized at the anode (94±4) compared to controls. FIG. 1 summarizes the fibroblast ingrowth results.

In the above examples, ingredients other than these recited can be added to achieve the desired result. Although particular examples have been shown and described above, modifications may be made, and it is intended in the claims to cover all modifications that come within the spirit and scope of the invention.

TABLE 1

Summary of histological data for electrically stimulated collagen sponges implanted in a excised dermal wound model. Mean number of fibroblasts per mm$^2$ is listed in column 5 with the standard deviation in parenthesis.

TABLE 1

Summary of histological data for electrically stimulated collagen sponges implanted in a excised dermal wound model. Mean number of fibroblasts per mm$^2$ is listed in column 5 with the standard deviation in parenthesis.

| Current | Polarity | Distance[1] | Generation | Fibroblasts |
|---|---|---|---|---|
| 0 | N/A | N/A | N/A | 125 (18) |
| 20 | Cathode | 1 | First | 130 (14) |
| 20 | Cathode | 2 | First | 142 (19) |
| 20 | Anode | 1 | First | 156* (22) |
| 20 | Anode | 2 | First | 156* (13) |
| 100 | Cathode | 1 | First | 194* (15) |
| 100 | Cathode | 1 | First | 152* (14) |
| 100 | Anode | 1 | First | 136 (25) |

TABLE 1-continued

Summary of histological data for electrically stimulated collagen sponges implanted in a excised dermal wound model. Mean number of fibroblasts per mm$^2$ is listed in column 5 with the standard deviation in parenthesis.

| Current | Polarity | Distance[1] | Generation | Fibroblasts |
|---|---|---|---|---|
| 100 | Anode | 2 | First | 139 (23) |
| 100 | Cathode | 1 | Second | 192* (51) |
| 100 | Cathode | 2 | Second | 180* (43) |
| 100 | Anode | 1 | Second | 108 (3) |
| 100 | Anode | 2 | Second | 94** (4) |

[1]Distance along electrode 1 = near circuit connections 2 = distal end of sponge
*Significantly greater than control
**Significantly less than control

REFERENCES

1. Fukada, E. Piezoelastic Properties of Biological Macromolecules, *Advances Biophys* 6, 121-155 (1974).
2. Bassett, C. A. L. Biophysical Principles Affecting Bone Structure, in: The Biochemistry and Physiology of Bone, Vol. II, Bourne, G. H., Ed., *Adacemic Press*, New York, 1971, 1.
3. Grodzinsky, A. J. Electromechanical and Physiochemical Properties of Connective Tissue, *CRC Critical Reviews in Biomedical Engineering* 9, 133-199 (1983).
4. Athenstaedt, H. Permanent Electric Polarization of the Meninges of Man, *Z. Zellforsh* 98, 300-322 (1969).
5. Marino, A. A. and Becker, R. O. The Effect of Electric Current on Rat Tail Tendon Collagen in Solution, *Calc. Tiss. Res.* 4, 330-338 (1970).
6. Murray, J. C. and Farndale, R. W. Modulation of Collagen Production in Cultured Fibroblasts by a Low-Frequency, Pulsed Magnetic Field. *Biochem. Biophys. Acta* 838, 98-105 (1985).
7. McLeod, K. J., Lee, R. C. and Ehrlich, H. P. Frequency Dependence of Electric Field Modulation of Fibroblast Protein Synthesis, *Science* 236, 1465-1468 (1987).
8. Yannas, I. V. and Burke, J. F. Design of an Artificial Skin. I. Basic design principles. *J. Biomed. Mater. Res.* 14, 65-81, (1980).
9. Doillon, C. J., Whyne, C. F., Berg, R. A., Olson, R. M. and Silver, F. H. Fibroblast-Collagen Sponge Interactions and the Spatial Deposition of Newly Formed Collagen Fibers In Vitro and In Vivo, *Scanning Electron Microscopy III*, 1313-1320 (1984).
10. Doillon, C. J., Whyne, C. F., and Berg, R. A. Fibroblast Growth on a Porous Collagen Sponge Containing Hyaluronic Acid and Fibronectin, *Biomaterials* 8, 195-200 (1987).
11. Doillon, C. J. and Silver, F. H. Collagen Wound Dressing: Effect of Hyaluronic Acid and Fibronectin, *Biomaterials* 7, 3-8 (1986).
12. Bassett, C. A. L., Mitchell, S. N. and Gaston, S. R. Treatment of Ununited Tibial Diaphyseal Fractures with Pulsing Electromagnetic Fields, *J. Bone Jt. Surg.* 63-A, 511-523 (1981).
13. Brighton, C. T., Black, J., Friedenberg, Z. B., Esterhai, J. L. Day, L. J. and Connolly, J. F. A Multicenter Study of the Treatment of Non-union with Constant Direct Current, *J. Bone Jt. Surg.* 63-A, 2-13 (1981).
14. DeHaas, W. G., Watson, J. and Morrison, D. M. Non-Invasive Treatment of Ununited Fractures of the Tibia Using Electrical Stimulation. *J. Bone. Jt. Surg.* 62-B, 465-470 (1980).
15. Lavine, L. S., Lustrin, I., Shomos, M. H., Rinaldi, R. A. and Liboff, A. R. Electric Enhancement of Bone Healing, *Science* 175, 1118-1121 (1972).
16. Assimacopoulos, D. Wound Healing Promotion by the Use of Negative Electric Current, *Am. Surg.* 34, 423-431 (1968).
17. Schauble, M. K., Habal, M. B., and Gullick, H. D. Inhibition of Experimental Tumor Growth in Hamsters by Small Direct Currents. *Arch. Pathol. Lab. Med.* 101, 294-297 (1977).
18. Konikoff, J. J. Electrical Promotion of Soft Tissue Repairs. *Ann. Biomed. Engng.* 4, 1-5 (1976).
19. Alvarez, O. M., Mertz, P. M. Smerbeck, R. V. and Eaglstein, W. H. The Healing of Superficial Skin Wounds is Stimulated by External Electrical Current. *J. Invest. Dermatol.* 81, 144-148 (1983).
20. Smith, J., Romansky, N., Vomero, J. and Davis, R. H. The Effect of Electrical Stimulation on Wound Healing in Diabetic Mice. *J. Amer. Podiatry Assoc.* 74, 71-75 (1984).
21. Assimacopoulos, D. Low Intensity Negative Electric Current in the Treatment of Ulcers of the Leg Due to Chronic Veinous Insufficiency. *Am. J. Surg.* 115, 683-687 (1968).
22. Wolcott, L. E., Wheeler, P. C., Hardwicke, H. M. and Rowley, B. A. Accelerated Healing of Skin by Electrotherapy: Preliminary Clinical Results. *Southern Med.* 62, 795-801 (1969).
23. Gault, W. R. and Gatens, P. F. Use of Low Intensity Direct Current in Management of Ischemic Skin Ulcers. *Phys. Ther.* 56, 265-269 (1976).
24. Komanowsky, M. Production of Comminuted Collagen for Novel Applications. *J. Am. Leather Chem.*, 69, 410-411 (1974).
25. Weadock, K., Olson, R. M. and Silver, F. H. Evaluation of Collagen Crosslinking Rechniques. *Biomater. Med. Devices Artif. Organs.* 11, 293-318 (1984).
26. Doillon, C. J., Whyne, C. F., Brandwein, S. and Silver, F. H. Collagen-Based Wound Dressings: Control of the Pore Structure and Morphology. *J. Biomed. Mater. Res.* 20, 1219-1228 (1986).
27. Friedenberg, Z., Andrews, E. T. Smolenski, B. I. Pearl, B. W. and Brighton, C. T. Bone Reaction to Various Amounts of Direct Current. *Surg. Gyn. Obstet.* 131, 894-899 (1970).
28. Junquiera, L. C. U., Bignolas G. and Bretani, R. R. Picro-Sirius Staining Plus Polarization Microscopy, A Specific Method for Collagen Detection in Tissue Sections. *Histochem. J.* 11, 477-455 (1979).
29. Doillon, C. J., Dunn, M. G., Berg, R. A. and Silver, F. H. Collagen Deposition During Wound Repair. *Scanning Electron Microscopy*, 11, 897-903 (1985).
30. Carey, L. C. and Lepley, L. D. Effect of Continuous Direct Electric Current on Healing Wounds. *Surg. Forum* 13, 33-36 (1962).
31. Wu, K. T., Go, N., Dennis, C., Enquist, I. F. and Sawyer, P. N. Effects of Electric Currents and Interfacial Potentials on Wound Healing. *J. Surg. Res.* 7, 122-128 (1967).
32. Frank, C. B., and Szeto, A. Y. J. A Review of Electromagnetically Enhanced Soft Tissue Healing. *IEEE Engineering in Medicine and Biology Magazine* 27-32 (12/1983).
33. Spadaro, J. A. Electrically Stimulated Bone Growth in Animals and Man. *Clinical Orthopeds. and Rel. Res.* 122, 325-332 (1977).
34. Zimmerman, M., Parsons, J. R., Alexander, H. and Weiss, A. B. The Electrical Stimulation of Bone Using a Filamentons Carbon Cathode. *J. Biomed. Mat. Res.* 18, 927–938 (1984).
35. Bassett, C. A. L. The Development and Application of Pulsed Electromagnetic Fields (PEMFs) for Ununited Fractures and Arthrodeses. *Orthoped. Clinics of North Am.* 15, 61–87 (1984).
36. Goodman, R., Basset, C. A. L., and Henderson, A. S. Pulsing Electromagnetic Fields Induce Cellular Transcription. *Science* 220, 1283–1285 (1983).
37. Leaper, D. J., Foster, M. E., Brennan, S. S. and Davies, P. W. An Experimental Study of the Influence of Magnetic Fields on Soft-Tissue Wound Healing. *J. of Trauma* 25, 1083–1084 (1985).
38. Gensler, W. Electrochemical Healing Similarities Between Animals and Plants. *Biophys. J.* 27, 461–466 (1979).
39. Carley, P. J. and Wainapel, S. F. Electrotherapy for Acceleration of Wound Healing: Low Intensity Direct Current. *Arch. Phys. Med. Rehab.* 66, 443–446 (1985).
40. Spadaro, J. A., Chase, S. E. and Webster, D. A. Bacterial Inhibition by Electrical Activation of Percutaneous Implants. *J. Biomed. Mat. Res.* 20, 565–577 (1986).
41. Cheng, N., VanHoof, H., Brockx, E., Hoogmartens, M. J., Mulier, J. C., DeDijcker, F. J. Sansen, W. M. and DeLoecker, W. The effects of electric currents on ATP generation, protein synthesis and membrane transport in rat skin. *Clin. Orth. Rel. Res.* 171, 264–572 (1982).
42. Brighton, C. T., Adler, S., Black, J., Itada, N., Friedenberg, Z. B. Cathodic oxygen consumption and electrically induced osteogenesis. *Clin. Orth. Rel. Res.* 107, 277–282 (1975).

We claim:

1. A therapeutic method for the treatment of wounds comprising dressing a wound with a biocompatible biodegradable collagen porous sponge product and applying cathodic low Intensity Direct Current (LIDC) through means for application of cathodic LID current, fibroblast ingrowth and collagen fiber alignment near the means for the application of the cathodic current.

2. The method of claim 1, wherein the LIDC is delivered via a cathodic LIDC.

3. The method of claim 2, wherein the current of the LIDC is at least about 20 microamps.

4. The method of claim 3, wherein the current of the LIDC is between about 20 and about 100 microamps.

5. The method of claim 2, wherein the LIDC is applied continuously.

6. The method of claim 5, wherein the LIDC is applied continuously until maximum wound healing is achieved.

7. The method of claim 1, which additionally comprises first dressing the wound with a biodegradable collagen flake or biodegradable powder product before dressing the wound with a biocompatible biodegradable collagen porous sponge product prior to the application of LIDC stimulation.

8. The method of claim 1 wherein the wound is a burn.

9. The method of claim 1, wherein the wound is a skin ulcer.

10. A therapeutic collagen dressing for the treatment of wound which comprises a biocompatible biodegradable collagen porous sponge product and means for the application of cathodic LIDC stimulation to promote fibroblast ingrowth and collagen fiber alignment near the means for the application of the cathodic current.

11. The dressing of claim 10, wherein the means for the application of LIDC stimulation is an electrode.

12. The dressing of claim 10, wherein the electrode is a cathode.

13. The dressing of claim 12, wherein the cathode is a carbon cathode.

14. The dressing of claim 13, wherein the carbon cathode is formed from carbon fibers.

15. The dressing of claim 14, wherein the carbon fibers are braided carbon fibers.

16. The dressing of claim 12, wherein the cathode is a metal cathode.

17. The dressing of claim 16, wherein the cathode metal is stainless steel.

18. The dressing of claim 16, wherein the cathode metal is a noble metal.

19. The dressing of claim 18, wherein the noble metal is selected from the group consisting of gold, silver, platinum and palladium.

20. The dressing of claim 12, wherein the cathode physical shape is selected from the group consisting of wire, plate and mesh.

21. The dressing of claim 10, wherein the means for the application of LIDC stimulation comprises metal particles dispersed throughout the implant in sufficient quantity to render the implant electrically conductive.

22. The dressing of claim 21, wherein the metal particles are stainless steel.

23. The dressing of claim 21, wherein the metal particles are noble metal particles.

24. The dressing of claim 23, wherein the noble metal particles are selected from the group consisting of gold, silver, platinum and palladium.

25. The dressing of claim 10, wherein the means for the application of LIDC stimulation is an electrolyte solution.

26. A biocompatible biodegradable collagen porous sponge product in a wound, said product having means for the application of cathodic LIDC stimulation to promote fibroblast ingrowth and collagen fiber alignment near the means for the application of the cathodic current.

27. The therapeutic collagen dressing of claim 10 which is an implant into the wound.

28. The therapeutic collagen dressing of claim 10 wherein the promotion of the collagen fiber alignment is in a biaxial orientation.

29. The therapeutic collagen dressing of claim 10 wherein means for the application of the cathodic stimulation is an electric current at least about 20 microamps.

30. The therapeutic collagen of claim 29 wherein the current is between about 20 and about 100 microamps.

31. The therapeutic collagen dressing of claim 10 wherein the means for cathodic stimulation are positioned externally to the wound dressing.

32. The therapeutic collagen dressing of claim 10 wherein the collagen product is constituted of collagen powder particles.

33. The therapeutic collagen dressing of claim 10 wherein the means for the application of the cathodic current promotes also increased fibroblast density near said means.

34. The therapeutic collagen dressing of claim 14 wherein the carbon fibers are inert and do not release metallic ions.

35. The therapeutic collagen dressing of claim 10 wherein the wound is a burn or skin ulcer.

* * * * *